United States Patent [19]

Niewöhner et al.

[11] Patent Number: 5,272,161
[45] Date of Patent: Dec. 21, 1993

[54] INDOLESULPHONAMIDE-SUBSTITUTED DIHYDROPYRIDINES

[75] Inventors: Ulrich Niewöhner, Wermelskirchen; Siegfried Goldmann; Ulrich Müller, both of Wuppertal; Andreas Knorr, Erkrath; Elisabeth Perzborn, Wuppertal; Matthias Schramm, Leverkusen; Bernhard Beckermann, Bergisch Gladbach, all of Fed. Rep. of Germany

[73] Assignee: Bayer Aktiengesellschaft, Leverkusen, Fed. Rep. of Germany

[21] Appl. No.: 942,550

[22] Filed: Sep. 9, 1992

[30] Foreign Application Priority Data

Sep. 20, 1991 [DE] Fed. Rep. of Germany ....... 4131346

[51] Int. Cl.$^5$ ................... C07D 401/12; A61K 31/44
[52] U.S. Cl. .................... 514/339; 514/333; 546/272; 546/256
[58] Field of Search ............... 514/339, 333; 546/272, 546/256

[56] References Cited

FOREIGN PATENT DOCUMENTS 0242518 2/1987 European Pat. Off. .
0247345 4/1987 European Pat. Off. .
0265947 10/1987 European Pat. Off. .

OTHER PUBLICATIONS

Wade, Jr. Organic Chemistry p. 349, 1987.
G. V. R. Born, *J. Physiol* 162, 1962; p. 67.
Th. Green, "Protective Groups in Organic Synthesis," 1981, whole book.
E. L. Eliel, *Stereochemistry of Carbon Compounds*, 1962, whole book.

*Primary Examiner*—Jane T. Fan
*Attorney, Agent, or Firm*—Sprung Horn Kramer & Woods

[57] ABSTRACT

Indolesulphonamide-substituted dihydropyridines can be prepared by reaction of dihydropyridinecarboxylic acids with hydroxy-substituted indolesulphonamides, or by reaction of amino- or hydroxy-substituted dihydropyridines with indolesulphonamidecarboxylic acids. The indolesulphonamide-substituted dihydropyridines can be employed as active substances in medicaments for the treatment of cardiac, circulatory and thromboedabolic disorders.

9 Claims, No Drawings

INDOLESULPHONAMIDE-SUBSTITUTED DIHYDROPYRIDINES

The invention relates to new indolesulphonamide-substituted dihydropyridines, processes for their preparation and their use in medicaments, in particular for cardiac, circulatory and thromboembolic disorders.

It has already been disclosed that 4-pyridyl- and 4-phenyl-1,4-dihydropyridine-3,5-dicarboxylates have a calcium-antagonistic and hypotensive action [cf. EP 265,947]. In addition, cycloalkano[1,2-b]indolesulphonamides are described in German Offenlegungsschrift 3,605,566.

The invention relates to new indolesulphonamide-substituted dihydropyridines of the general formula (I)

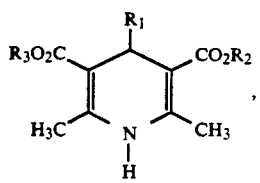

in which
R$_1$ represents aryl having 6 to 10 carbon atoms or a 5- to 7-membered unsaturated heterocycle having up to 2 heteroatoms from the series comprising S, N and O, each of which is optionally mono-substituted to trisubstituted by identical or different substituents from the series comprising halogen, nitro, trifluoromethyl, trifluoromethoxy, cyano, difluoromethoxy, straight-chain or branched alkyl, alkoxy or alkylthio each having up to 8 carbon atoms, benzyl and phenoxy, R$_2$ represents a radical of the formula

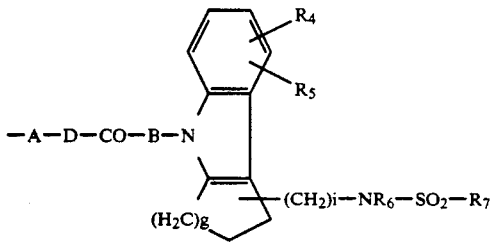

in which
A and B are identical or different and denote a group of the formula —(CH$_2$)$_b$—(CR$_8$R$_9$)$_d$—(CH$_2$)$_e$, in which
b denotes a number 1, 2, 3, 4 or 5,
d and e are identical or different and denote a number 0, 1, 2, 3, 4 or 5,
R$_8$ and R$_9$ are identical or different and denote hydrogen or straight-chain or branched alkyl having up to 6 carbon atoms,
D denotes an oxygen atom or the —NH group,
g denotes a number 1 or 2,
i denotes a number 0, 1, 2 or 3,
R$_4$ and R$_5$ are identical or different and denote hydrogen, aryl having 6 to 10 carbon atoms, nitro, cyano, halogen, trifluoromethyl, trifluoromethoxy, carboxyl, hydroxyl or straight-chain or branched alkyl, alkoxy or alkoxycarbonyl each having up to 6 carbon atoms,
R$_6$ denotes hydrogen, straight-chain or branched alkyl having up to 8 carbon atoms or phenyl,
R$_7$ denotes aryl having 6 to 10 carbon atoms or a 5- to 7-membered unsaturated heterocycle having up to 2 heteroatoms from the series comprising S, N and O, each of which is optionally monosubstituted to tri-substituted by identical or different substituents from the series comprising halogen, cyano, nitro, trifluoromethyl, trifluoromethoxy, trifluoromethylthio, hydroxyl, carboxyl, phenyl, phenoxy, benzyloxy, benzylthio, straight-chain or branched alkoxy, alkyl, carboxyalkyl, alkoxycarbonyl and alkoxycarbonylalkyl each having up to 8 carbon atoms or by a group of the formula —NR$_{10}$R$_{11}$, in which
R$_{10}$ and R$_{11}$ are identical or different and denote hydrogen, straight-chain or branched alkyl having up to 6 carbon atoms, phenyl or benzyl, R$_3$ represents straight-chain or branched alkyl or alkenyl each having up to 10 carbon atoms, each of which is optionally monosubstituted or disubstituted by identical or different substituents from the series comprising carboxyl, straight-chain or branched alkylthio, alkoxy, alkoxycarbonyl, acyl or acyloxy each having up to 8 carbon atoms, phenyl, phenoxy, carboxyl and hydroxyl or by the group —NR$_{10}$R$_{11}$, in which
R$_{10}$ and R$_{11}$ have the abovementioned meaning,
or represents the group of the formula

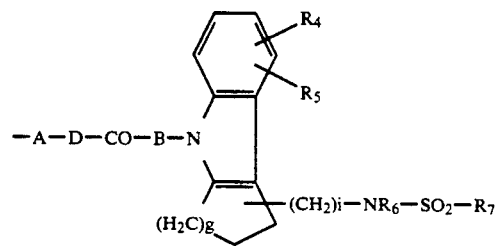

in which
A, B, D, g, i, R$_4$, R$_5$, R$_6$ and R$_7$ and have the abovementioned meaning,
if appropriate in an isomeric form, and their salts.

The compounds of the general formula (I) according to the invention have several asymmetric carbon atoms and can therefore occur in various stereochemical forms which either behave as image and mirror image (enantiomers), or which do not behave as image and mirror image (diastereomers). The invention relates both to the antipodes and to the racemic forms as well as the diastereomer mixtures. Like the diastereomers, the racemic forms can also be separated in a known manner into the stereoisomerically uniform constituents (cf. E. L. Eliel, Stereochemistry of Carbon Compounds, McGraw Hill, 1962).

The substances according to the invention can also exist as salts. In the context of the invention physiologically acceptable salts are preferred.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

Salts in the context of the present invention are additionally salts of the univalent metals, such as alkali metals, and the ammonium salts. Sodium, potassium and is ammonium salts are preferred.

Heterocycle in general represents a 5- to 7-membered, preferably 5- to 6-membered unsaturated ring, which as heteroatoms can contain up to 2 oxygen, sulphur and/or nitrogen atoms. 5- and 6-membered rings containing one oxygen, sulphur and/or up to 2 nitrogen atoms are preferred. The following are preferably mentioned: thienyl, furyl, pyrrolyl, pyridyl or pyrimidyl.

Preferred compounds of the general formula (I) are those in which $R_1$ represents phenyl, naphthyl, o-pyridyl, m-pyridyl, p-pyridyl or thienyl, each of which is optionally monosubstituted or disubstituted by identical or different substituents from the series comprising fluorine, chlorine, bromine, nitro, trifluoromethyl, trifluoromethoxy, straight-chain or branched alkyl or alkoxy each having up to 6 carbon atoms, benzyl and phenoxy, represents a radical of the formula $R_2$ represents a radical of the formula

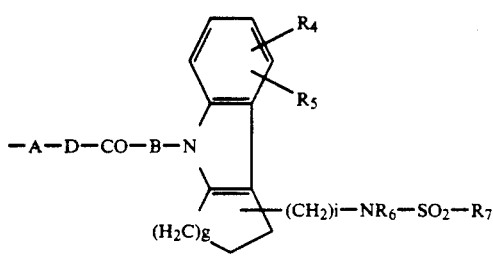

in which

A and B are identical or different and denote a group of the formula $—(CH_2)_b—(CR_8R_9)_d—(CH_2)_e$, in which b denotes a number 1, 2, 3 or 4, d and e are identical or different and denote a number 0, 1, 2 or 3, $R_8$ and $R_9$ are identical or different and denote hydrogen or straight-chain or branched alkyl having up to 4 carbon atoms, D denotes an oxygen atom or the —NH group, g denotes a number 1 or 2, i denotes a number 0, 1 or 2, $R_4$ and $R_5$ are identical or different and denote hydrogen, phenyl, nitro, cyano, fluorine, chlorine, bromine, trifluoromethyl or straight-chain or branched alkyl or alkoxy each having up to 4 carbon atoms, $R_6$ denotes hydrogen or straight-chain or branched alkyl having up to 6 carbon atoms, $R_7$ denotes phenyl, naphthyl or thienyl, each of which is optionally monosubstituted or disubstituted by identical or different substituents from the series comprising fluorine, chlorine, trifluoromethyl, trifluoromethoxy, hydroxyl and carboxyl or by straight-chain or branched alkoxy, alkyl or alkoxycarbonyl each having up to 6 carbon atoms or by a group of the formula $—NR_{10}R_{11}$, in which $R_{10}$ and $R_{11}$, are identical or different and denote hydrogen, straight-chain or branched alkyl having up to 4 carbon atoms, phenyl or benzyl, $R_3$ represents straight-chain or branched alkyl having up to 8 carbon atoms, which is optionally substituted by straight-chain or branched alkoxy, alkylthio, alkoxycarbonyl, acyl or acyloxy each having up to 6 carbon atoms, phenyl, phenoxy, carboxyl or hydroxyl or by the group $—NR_{10}R_{11}$, in which $R_{10}$ and $R_{11}$ have the abovementioned meaning, or represents the group of the formula

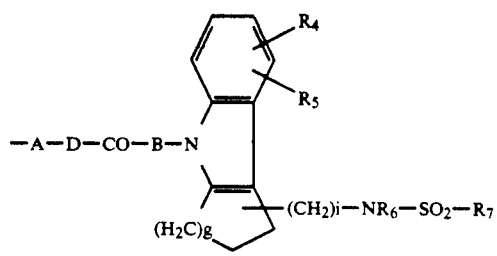

in which

A, B, D, g, i, $R_4$, $R_5$, $R_6$ and $R_7$ have the abovementioned meaning, if appropriate in an isomeric form, and their salts.

Particularly preferred compounds of the general formula (I) are those in which $R_1$ represents phenyl, naphthyl, m-pyridyl or thienyl, each of which is optionally monosubstituted or disubstituted by identical or different substituents from the series comprising fluorine, chlorine, nitro, trifluoromethyl, trifluoromethoxy, straight-chain or branched alkyl or alkoxy each having up to 4 carbon atoms, benzyl and phenoxy, $R_2$ represents a radical of the formula

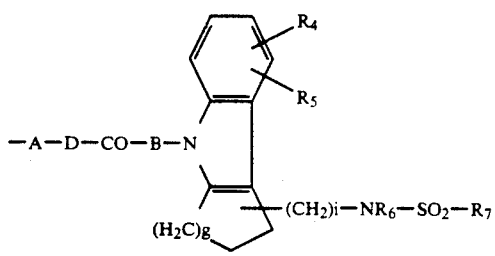

in which

A and B are identical or different and denote a group of the formula $—(CH_2)_b—(CR_8R_9)_d—(CH_2)_e$, in which b denotes a number 1, 2 or 3, d and e are identical or different and denote a number 0, 1 or 2, $R_8$ and $R_9$ are identical or different and denote hydrogen, methyl or ethyl, D denotes an oxygen atom or the —NH group, g denotes a number 1 or 2, i denotes a number 0 or 1, $R_4$ and $R_5$ are identical or different and denote hydrogen, phenyl, nitro, fluorine, chlorine, trifluoromethyl, methyl or methoxy, $R_6$ denotes hydrogen or straight-chain or branched alkyl having up to 4 carbon atoms, R7 denotes phenyl, naphthyl or thienyl, each fluorine, chlorine, trifluoromethyl or trifluoromethoxy or by straight-chain or branched alkoxy or alkyl each having up to 4 carbon atoms, R3 represents straight-chain or branched alkyl having up to 6 carbon atoms, which is optionally substituted by straight-chain or branched alkoxy, alkylthio, alkoxycarbonyl or acyl each having up to 4 carbon atoms, phenyl or phenoxy, or represents the group of the formula

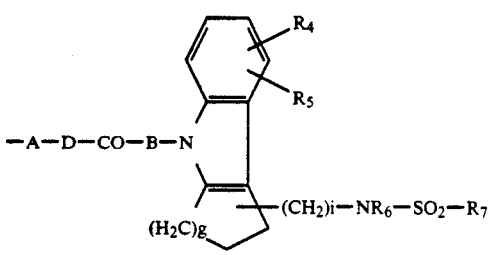

in which

A, B, D, g, i, R4, R5, R6 and R7 have the abovementioned meaning, if appropriate in an isomeric form, and their salts.

Very particularly preferred compounds of the general formula (I) are those in which R1 represents phenyl or pyridyl, each of which is optionally substituted by fluorine, chlorine, nitro or trifluoromethyl, R2 represents a radical of the formula

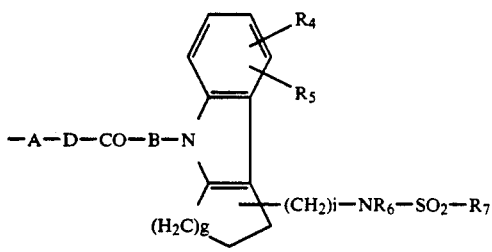

in which

A denotes a group of the formula $-(CH_2)_b-(CR_8R_9)_d-(CH_2)_e$, where b represents a number 1, 2 or 3, d and e are identical or different and represent a number 0, 1 or 2, R8 and R9 are identical or different and represent hydrogen or methyl, D denotes an oxygen atom or an NH group, g denotes the number 2, i denotes the number 0, R4 and R5 denote hydrogen, R6 denotes hydrogen, R7 denotes phenyl which is optionally substituted by fluorine or chlorine, R3 represents straight-chain or branched alkyl having up to 6 carbon atoms, or a group of the formula

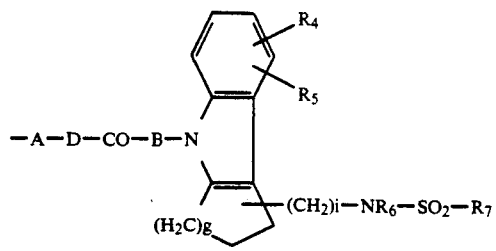

in which

A, B, D, g, i, R4, R5, R6 and R7 have the abovementioned meaning, if appropriate in an isomeric form, and their salts.

In addition, processes for the preparation of the compounds of the general formula (I) according to the invention have been found, characterised in that

[A] dihydropyridinecarboxylic acids of the general formula (II)

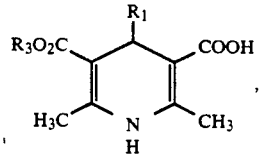

in which

R1 and R3 have the abovementioned meaning, are esterified with indolesulphonamides of the general formula (III)

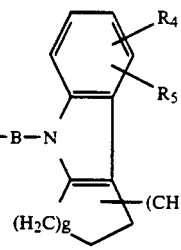

in which

A, D, B, g, i, I R4, R5, R6 and R7 have the abovementioned meaning, in inert solvents, if appropriate in the presence of a base and/or of an auxiliary, and if appropriate with activation of the carboxylic acid, or in that

[B] dihydropyridines of the general formula (IV)

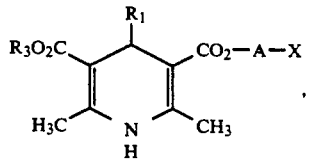

in which

R1, R3 and A have the abovementioned meaning and x either represents an —OH group if D denotes an oxygen atom, or represents an —NH2 group if D denotes an —NH group, are condensed with indolesulphonamide acids of the general formula (V)

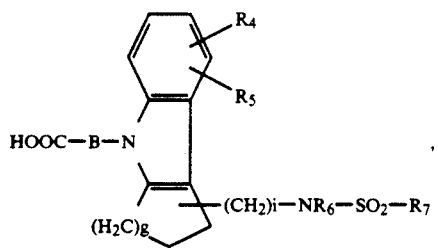

in which

B, g, i, $R_4$, $R_5$, $R_6$ and $R_7$ have the abovementioned meaning, in inert solvents, if appropriate in the presence of an auxiliary and if appropriate with activation of the carboxylic acid, and in the case of the pure enantiomers, separation of the enantiomers is first carried out according to a customary method at the stage of the acids of the general formula (II) and the corresponding enantiomerically pure acids are reacted with the enantiomerically pure compounds of the general formula (III) likewise obtained after a separation of the diastereomers in the course of the synthesis or, after conversion of the enantiomerically pure acids (II) into the enantiomerically pure compounds (IV), with the enantiomerically pure compounds of the general formula (V).

The processes according to the invention can be illustrated by way of example by the following equations:

[B]

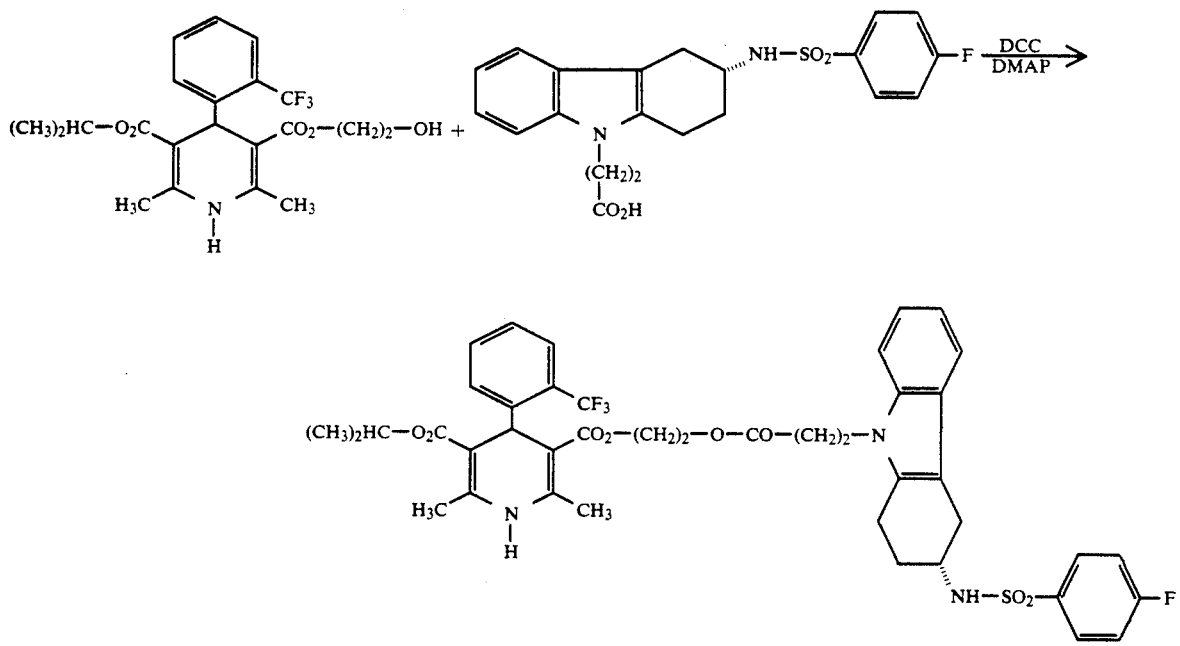

[A]

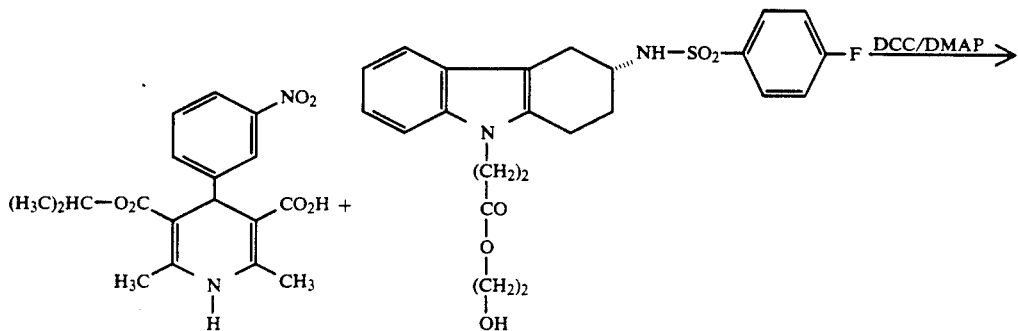

-continued
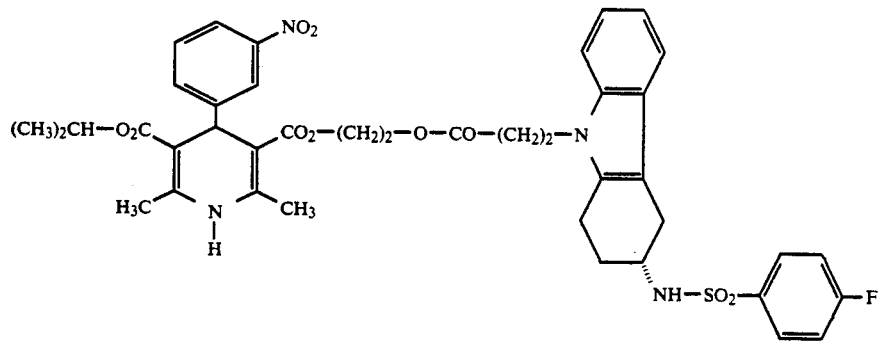
[A]
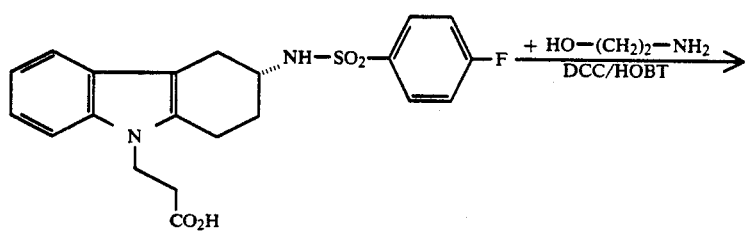
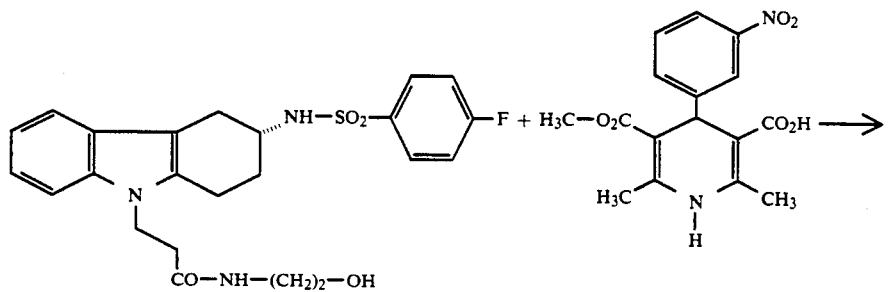
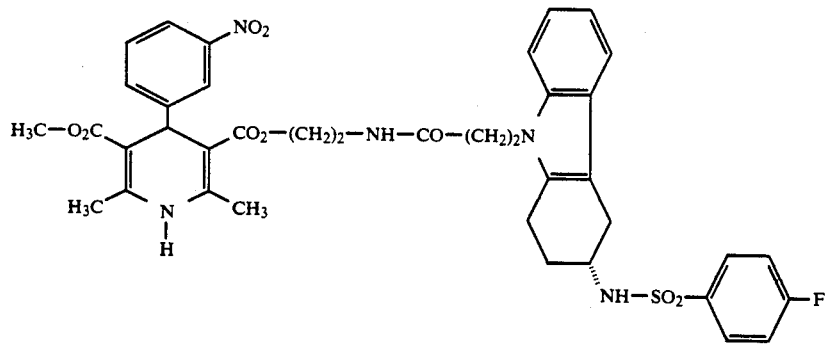
[B]
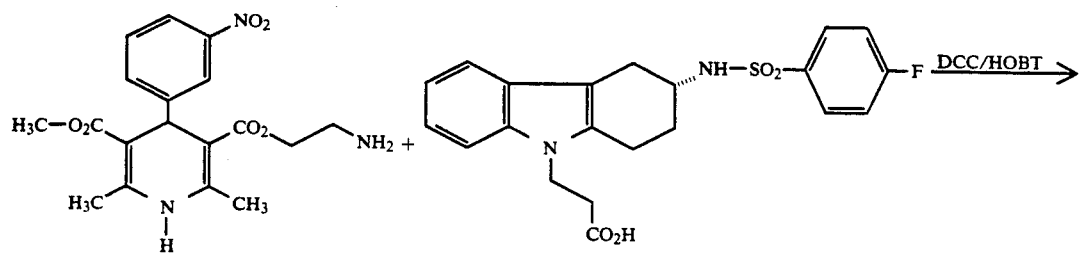

-continued

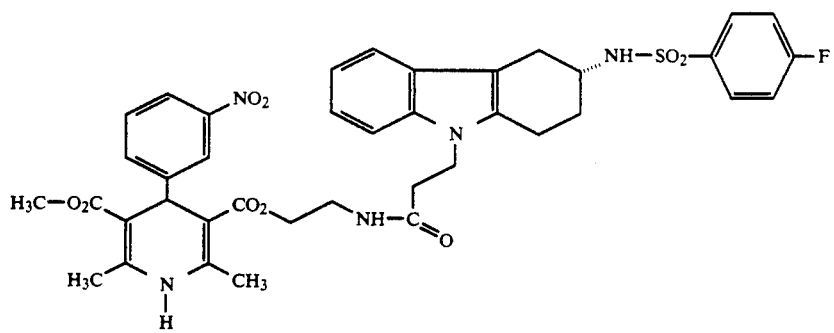

Solvents for processes [A] and [B] according to the invention can in this case be inert organic solvents which do not change under the reaction conditions. These preferably include ethers such as, for example, diethyl ether, dioxane, tetrahydrofuran, glycol monomethyl ether or glycol dimethyl ether, halogenohydrocarbons such as di-, tri- or tetrachloromethane, dichloroethylene, trichloroethylene, ethyl acetate, toluene, acetonitrile, hexamethylphosphoric triamide and acetone. Of course, it is possible to employ mixtures of the solvents. Tetrahydrofuran is preferred.

The auxiliaries employed are preferably condensing agents which can also be bases. Those preferred here are the customary condensing agents such as carbodiimides, for example N,N'-diethyl-, N,N'-dipropyl-, N,N'-diisopropyl- or N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphonate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphonate. N,N'-Dicyclohexylcarbodiimide and carbonyldiimidazole are preferred.

Suitable bases are in general alkali metal carbonates such as, for example, sodium carbonate or potassium carbonate, or organic bases such as trialkylamines, for example triethylamine, N-ethylmorpholine, N-methylpiperidine or diisopropylethylamine, or dimethylaminopyridine, 1,8-diazabicyclo[5.4.0]undec-7-ene (DBU) or 1,5-diazabicyclo[4.3.0]non-5-ene (DBN). Dimethylaminopyridine is preferred.

The base is in general employed in an amount from 0.01 mol to 1 mol, preferably from 0.05 mol to 0.1 mol, in each case relative to 1 mol of the compounds of the general formula (II) or (IV).

The auxiliaries are in general employed in an amount from 1 mol to 3 mol, preferably from 1 mol to 1.5 mol, in each case relative to 1 mol of the compounds of the general formulae (II) and (IV).

The reaction temperature for processes [A] and [B] can be varied within a substantial range. In general, the reaction is carried out in a range from −20° C. to 200° C., preferably from 0° C. to 25° C.

The processes can be carried out at normal pressure, elevated pressure or reduced pressure (for example from 0.5 to 5 bar), preferably at normal pressure.

When carrying out the processes according to the invention, any desired ratio of the substances participating in the reaction can be used. In general, however, the reaction is carried out with molar amounts of the reactants.

To activate the carboxylic acid, the customary reagents such as inorganic halides, for example thionyl chloride, phosphorus trichloride or phosphorus pentachloride, or carbonyldiimidazole, carbodiimides such as cyclohexylcarbodiimide or 1-cyclohexyl-3-[2-(N-methylmorpholino)ethyl]-carbodiimide p-toluenesulphonate or N-hydroxyphthalimide or N-hydroxy-benzotriazole are suitable.

Enantiomerically pure forms are additionally obtained, for example, by separating mixtures of the diastereomers of the compounds of the general formula (I) in which $R^2$ or $R^3$ represents an optical ester radical according to a customary method, then preparing the enantiomerically pure carboxylic acids and then converting the latter, if appropriate by esterification with appropriate alcohols, into the enantiomerically pure dihydropyridines.

Suitable chiral ester radicals are all esters of enantiomerically pure alcohols such as, for example, 2-butanol, 1-phenylethanol, tactic acid, tactic acid esters, mandelic acid, mandelic acid esters, 2-amino alcohols, sugar derivatives and many other enantiomerically pure alcohols.

The diastereomers are in general separated either by fractional crystallisation, by column chromatography or by Craig partition. Which is the optimum method must be decided from case to case; sometimes it is also expedient to use combinations of the individual processes. Separation by crystallisation or Craig partition or a combination of both methods is particularly suitable.

The enantiomerically pure dihydropyridines are preferably esterified in ethers such as diethyl ether or tetrahydrofuran, dimethylformamide, methylene chloride, chloroform, acetonitrile or toluene.

Preferably, the enantiomers of the compounds of the general formula (II) are separated by column chromatography according to a customary method, the columns being packed with chiral support materials.

The above preparation processes are only indicated for purposes of clarification. The preparation of the compounds of the formula (I) is not restricted to these processes, but any modification of these processes is applicable in the same manner to the preparation of the compounds according to the invention.

The compounds of the general formula (IV) are largely known [cf. U.S. Pat. No. 4,419,518] or can be prepared by the methods customary in dihydropyridine chemistry, for example with activation of the respective carboxylic acids using one of the abovementioned auxiliaries, preferably dicyclohexylcarbodiimide or carbonyldiimidazole, and subsequent reaction with compounds of the general formula (VI)

HO—A—X         (VI)

in which

A and X have the abovementioned meaning.

The compounds of the general formula (V) are known [cf. German Offenlegungsschrift 3,605,566].

The compounds of the general formula (II), in the case in which $R^3$ represents the radical of the formula

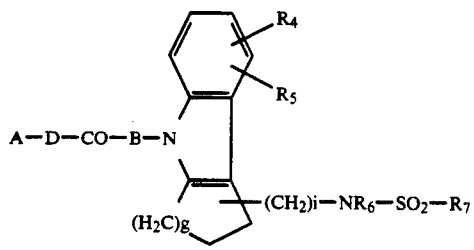

in which

A, B, D, $R_4$, $R_5$, $R_6$, $R_7$, g and i have the abovementioned meaning, are new and can be prepared by the method indicated under [A].

The compounds of the general formula (III) are new and can be prepared by first activating the carboxylic acid function in the compounds of the general formula (V), if appropriate in the presence of one of the abovementioned bases and/or auxiliaries, preferably with dicyclohexylcarbodiimide and dimethylaminopyridine, then reacting them with compounds of the general formula (VII)

EO—A—OH         (VII)

in which

A has the abovementioned meaning and

E represents a typical hydroxyl protective group, preferably benzyl, in inert solvents, in the presence of a base, and in a last step removing the latter according to a customary method.

Suitable solvents are the abovementioned solvents, preferably tetrahydrofuran and methylene chloride.

Suitable bases are alkali metal and alkaline earth metal hydroxides, such as sodium hydroxide or potassium hydroxide. Sodium hydroxide is preferred.

The base is employed in an amount from 0.01 mol to 1 mol, preferably from 0.05 mol to 0.15 mol, relative to 1 mol of the compound of the general formula (V).

The reaction temperature can be varied within a substantial range. In general, the reaction is carried out in a range from −20° C. to 200° C., preferably from 0° C. to 25° C.

The processes can be carried out at normal pressure, elevated pressure or reduced pressure (for example from 0.5 to 5 bar), preferably at normal pressure.

Hydroxyl protective group in the context of the abovementioned definition in general represents a protective group from the series comprising: trimethylsilyl, triethylsilyl, triisopropylsilyl, tert-butyl-dimethylsilyl, triphenylsilyl or benzyl. Trimethylsilyl, tert-butyldimethylsilyl or benzyl is preferred.

The protective groups are removed from the corresponding ethers according to a customary method, for example by hydrogenolytic cleavage of the benzyl ethers in the abovementioned inert solvents in the presence of a catalyst using hydrogen gas [cf. additionally Th. Green: "Protective Groups in Organic Synthesis", J. Wiley & Sons, 1981, New York].

The compounds of the general formulae (VI) and (VII) are known per se or can be prepared by a customary method [cf. Beilstein 1 467; 1, 2, 519].

The compounds of the general formula (I) according to the pharmacological action. On the one hand, they influence the contractility of the heart, the tone of the smooth musculature and the electrolyte and liquid balance. In addition, they have a platelet aggregation-inhibiting and thromboxane $A_2$ antagonistic action. They can therefore be employed in medicoments for the treatment of pathologically changed blood pressure and of cardiac insufficiency, and also as coronary therapeutics. They can be employed for the treatment of thromboembolic disorders and ischaemias such as myocardial infarct, stroke, transitory and ischaemic attacks, angina pectoris, peripheral circulatory disorders, prevention of restenoses such as after thrombolysis therapy, percutaneous transluminal angioplasties (PTA), percutaneous transluminal coronary angioplasties (PTCA), by-pass and for the treatment of arteriosclerosis, asthma and allergies.

The substances were investigated for their hypotensive action in the conscious rat. In conscious rats having high blood pressure due to genetic causes ("spontaneously hypertensive rats" of the Okamoto strain), the arterial blood pressure is measured in a bloodless manner using the "tail cuff" at defined time intervals after administration of substance. The substances to be tested are administered in various doses intragastrally ("orally") suspended in a Tylose suspension by stomach tube. The compounds according to the invention reduce the arterial blood pressure of the hypertensive rats at a clinically relevant dosage.

The following actions resulted:

SH rat: blood pressure reduction > 15 mm

| Ex. No. | mg/kg |
| --- | --- |
| 2 | 100 |
| 10 | 100 |
| 15 | 100 |
| 31 | 100 |

In these rats, the inhibition of platelet aggregation ex vivo (rat) was also investigated by the following method.

The test substances or solvents are administered to rats by means of a stomach tube. After 60 minutes, blood is taken from the animals under ether anaesthesia via the abdominal aorta. The blood is taken up in 3.8% strength citrate solution (9+1). Platelet-rich plasma (PRP) is then obtained by centrifugation at 150 g for 20 minutes. 3 parts of PRP are diluted with 1 part of 0.9% NaCl and preincubated at 37° C. for 5 minutes. Platelet aggregation is determined by the turbidometric method (cf. Born, G.V.R.; J. Physiol. 162, 67, 1962] in an aggregometer at 37° C. For this purpose, PRP is mixed with collagen, an aggregation-inducing agent. Testing is in each case carried out at threshold concentrations of collagen which cause maximum aggregation in the control batch. The change in the optical density of the aggregating sample is recorded and the maximum result is determined. For this purpose, the percentage inhibition compared with the control is calculated. An inhibition of more than 50% resulted.

The new active substances can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient to achieve the dosage range indicated.

The formulations are prepared, for example, by extending the active substances with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular prelingually or intravenously.

In general, it has proved advantageous on intravenous administration to administer amounts from about 0.01 to 10 mg/kg, preferably about 0.1 to 3 mg/kg, of body weight to achieve effective results, and on oral administration the dosage is about 0.01 to 20 mg/kg, preferably 0.1 to 10 mg/kg of body weight.

In spite of this, it may be necessary to depart from the amounts mentioned, in particular depending on the body weight or the type of administration route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of the administration of relatively large amounts, it may be advisable to divide these into several individual doses over the course of the day.

Eluents a) Toluene:ethyl acetate=4:1 b) Dichloromethane:methanol=20:1 c) Toluene:ethyl acetate=1:1 d) Toluene:ethyl acetate=1:2 e) Toluene:ethyl acetate=2:1 f) Dichloromethane:petroleum ether=3:1 g) Petroleum ether:ethyl acetate=1:1 h) Toluene:ethyl acetate=1:5 i) Petroleum ether:ethyl acetate=2:3 j) Cyclohexane:ethyl acetate=1:1 k) Toluene:acetone=5:1

STARTING COMPOUNDS

Example I

Ethyl 4-(3-chlorophenyl)-5-(2-hydroxyethoxycarbonyl)-2,6-dimethyl-1,4-dihydropyridine-3-carboxylate

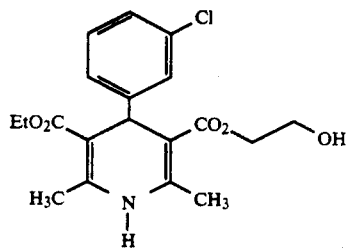

3.4 g (10 mmol) of 4-(3-chlorophenyl)-3-(ethoxycarbonyl)-2,6-dimethyl-1,4-dihydropyridine-5-carboxylic acid and 2 g (10 mmol) of carbonyldiimidazole are stirred overnight at room temperature in 50 ml of abs. THF. The mixture is evaporated, the residue is taken up in 50 ml of ethyl acetate and the mixture is washed twice with 50 ml of water each time. After drying over $Na_2SO_4$, the solvent is distilled off and the residue (3.55 g) is dissolved in 10 ml of abs. THF. After addition of 100 ml of ethylene glycol and 100 mg of NaH, the mixture is stirred at room temperature for 3 h, mixed with 100 ml of ethyl acetate and extracted twice by shaking with 100 ml of water each time. After drying over sodium sulphate, the extract is evaporated. The residue is homogeneous in the TLC and is further processed directly. Yield: 2.95 g (83% of theory)

Example II

Benzylethylene glycol (3R)-3-(4-fluorophenylsulphonyl-amido)-1,2,3,4-tetrahydrocarbazole-9-propanoate

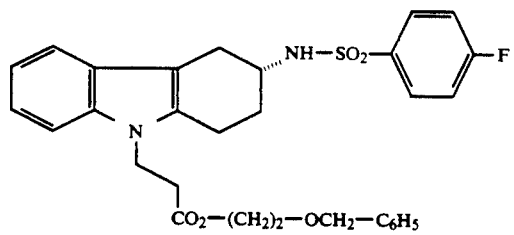

16.7 g (0.11 mol) of monobenzylethylene glycol, 22.7 g (0.11 mol) of dicyclohexylcarbodiimide and 1 g of DMAP are added successively at 0° C. to a solution of 41.6 g (0.1 mol) of (3R)-3-(4-fluorophenylsulphonamido)-1,2,3,4-tetrahydrocarbazole-9-propanoic acid in 500 ml of methylene chloride. The mixture is stirred at 0° C. for 30 minutes, then at room temperature for 2 h, filtered and washed twice with 1N NAOH and once with 1M HCl. After drying over $Na_2SO_4$, the methylene chloride is distilled off and the residue is purified through a short column by flash chromatography (eluent: toluene/acetone 20:4).

Yield: 51.7 g (94% of theory)

Example III

Ethylene glycol (3R)-3-(4-fluorophenylsulphonamido)-1,2,3,4-tetrahydrocarbazole-9-propanoate

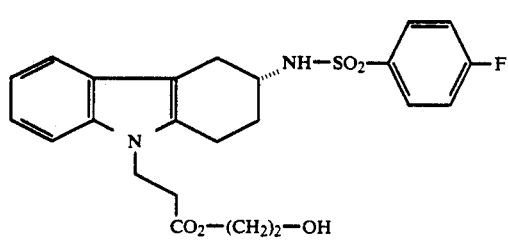

55 g (0.1 mol) of the compound from Example II are hydrogenated in 800 ml of abs. THF with 15 g of 10% strength palladium/C at 50 bar and 20° C. for 12 h. The catalyst is filtered off, the solvent is distilled off and the residue is purified by flash chromatography (eluent: toluene/acetone 10:1 to 5:1).

Yield: 29.5 g (64.1% of theory) $R_f=0.48$ (toluene/acetone 1:1)

Example IV

N-(2-Hydroxyethyl) (3R)-3-(4-fluorophenylsulphonylamido)-1,2,3,4-tetrahydrocarbazole-9-propionamide

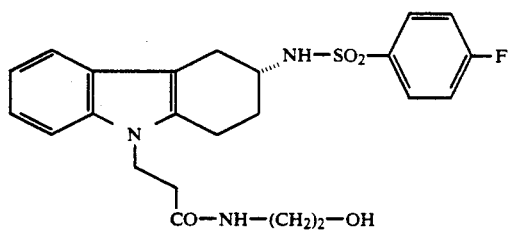

41.6 g (0.1 mol) of (3R)-3-(4-fluorophenylsulphonamido)-1,2,3,4-tetrahydrocarbazole-9-propanoic acid and 13.5 g (0.1 mol) of 1-hydroxybenzotriazole are dissolved in 500 ml of abs. $CH_2Cl_2$ and treated at 0° C. with 22.7 g (0.11 mol) of dicyclohexylcarbodiimide. The mixture is stirred at 0° C. for 1 h and at 200° C. for 1 h. 6.1 g (0.1 mol) of 2-aminoethanol in 20 ml of abs. $CH_2Cl_2$ are then added dropwise and the mixture is stirred at 20° C. for 3 h. The precipitate is filtered off, and the $CH_2Cl_2$ phase is washed with 1N NAOH, 1N HCl and saturated NaCl solution. After drying over $Na_2SO_{4l}$ the solvent is distilled off and the residue is purified by flash chromatography (eluent: toluene/acetone 4:1 to 2:1).

$R_f=0.36$ (toluene/acetone 1:1)

Example V 4-(3-Trifluoromethylphenyl)-3-methoxycarbonyl-5-(2-phthalimidomethoxycarbonyl)-2,6-dimethyl-1,4-dihydropyridine

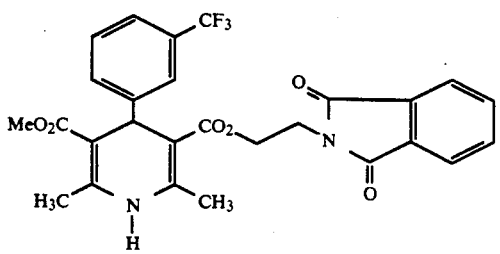

3.6 g (10 mmol) of 4-(3-trifluoromethylphenyl)-3-methoxycarbonyl-2,6-dimethyl-1,4-dihydropyridine-5-carboxylic acid and 2 g (10 mmol) of carbonyldiimidazole are stirred overnight at room temperature in 50 ml of abs. THF. The mixture is evaporated, the residue is taken up in 50 ml of ethyl acetate and the mixture is washed twice with 50 ml of water each time. After drying over $Na_2SO_4$, the solvent is distilled off and the residue (3.7 g) is dissolved in 100 ml of abs. THF. After addition of 1.91 g (10 mmol) of N-(2-hydroxyethyl)-phthalimide and 300 mg of NaH, the mixture is stirred at room temperature for 3 h. It is evaporated and the residue is chromatographed on silica gel using toluene/acetone 10:1 as the eluent.

$R_f=0.58$ (tol/ac 1:1)

Yield: 3.14 g (59.5% of theory)

Example VI 4-(3-Trifluoromethylphenyl)-3-methoxycarbonyl-5-(2-aminoethoxycarbonyl)-1,4-dihydropyridine

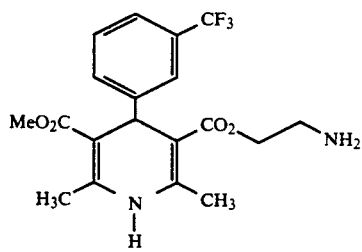

2.64 g (5 mmol) of the compound from Example V and 1.5 g of hydrazine hydrate are boiled under reflux for 1 h in 50 ml of ethanol. The mixture is filtered hot, cooled, filtered again and evaporated. The residue is chromatographed on silica gel using $CH_2Cl_2$/MeOH 10:1 as the eluent.

$R_f=0.27$ ($CH_2Cl_2$/MeOH 10:1)

Yield: 1.27 g (63.8% of theory)

PREPARATION EXAMPLES

Method B

General working procedure for preparation of the compounds of the general formula (I) in which D represents an oxygen atom, by esterification of various DHP ethylene glycol esters of the general formula (IV) with the compounds of the general formula (V).

7 mmol of DHP ethylene glycol ester and 2.91 g (7 mmol) of (3R)-3-(4-fluorophenylsulphonamido)-1,2,3,4- tetrahydrocarbazole-9-propionic acid are dissolved in 20 mmol of abs. THF. 100 mg of DMAP and 1.87 g (9.1 mmol) of dicyclohexylcarbodiimide are added at 0° C. The mixture is stirred at 0° C. for 30 min, then at 20° C. for 3 h. The precipitate is filtered off, the THF is distilled off and the residue is taken up in 50 ml of ethyl acetate. It is extracted twice by shaking with saturated aq. $Na_2CO_3$ solution, once with 1N HCl and once with saturated NaCl solution, and the organic phase is dried over $Na_2SO_4$ and evaporated. The residue is purified by chromatography (eluent: toluene/acetone mixtures 25:1 to 5:1).

Method A

General working procedure for preparation of the compounds of the general formula (I) in which D represents an oxygen atom, by esterification of various DHP hemiesters of the general formula (II) with ethylene glycol (3R)-3-(4-fluorophenylsulphonamido)-1,2,3,4-tetrahydrocarbazole-9-propanoate (compound from Example III).

7 mmol of DHP hemi-ester and 3.22 g (7 mmol) of the compound from Example III are dissolved in 20 ml of abs. THF. 100 mg of DMAP and 1.87 g (9.1 mmol) of dicyclohexylcarbodiimide are added at 0° C. The mixture is stirred at 0° C. for 30 min, then at 20° C. for 3 h. The precipitate is filtered off, the THF is distilled off and the residue is taken up in 50 ml of ethyl acetate. The mixture is extracted twice by shaking with saturated aq. $Na_2CO_3$ solution, once with 1N HCl and once with saturated NaCl solution, and the organic phase is dried over $Na_2SO_4$ and evaporated. The residue is purified by chromatography (eluent: toluene/acetone mixtures 25:1 to 5:1).

The compounds listed in Tables 1, 2 and 3 are prepared by the general preparation procedures indicated above:

TABLE 1

| Ex. No. | Y | $R_3$ | Yield (% of theory) | $R_f$ (eluent) |
|---|---|---|---|---|
| 1 | o-$CF_3$ | —$CH(CH_3)_2$ | 61.5 | 0.28 (c) |
| 2 | m-$NO_2$ | —$C_2H_5$ | 66.4 | 0.39 (e) |
| 3 | m-$NO_2$ | —$CH(CH_3)_2$ | 86.1 | 0.15 (a) |
| 4*2 | m-$NO_2$ | —$CH(CH_3)_2$ | 89.3 | 0.15 (a) |
| 5*2 | m-$NO_2$ | —$CH(CH_3)_2$ | 77.0 | 0.15 (a) |
| 6 | m-$NO_2$ | -n-$C_5H_{11}$ | 64.3 | 0.68 (i) |
| 7 | m-$NO_2$ | -n-$C_6H_{13}$ | 59.8 | 0.48 (g) |
| 8 | m-$NO_2$ | [structure shown] | 42.4 | 0.38 (f) |
| 9 | m-$NO_2$ | —$C(CH_3)_3$ | 50.6 | 0.55 (c) |
| 10 | m-$NO_2$ | —$(CH_2)_2$—$OCH_3$ | 55.8 | 0.51 (c) |
| 11 | m-$NO_2$ | —$CH_2$—$C_6H_5$ | 32.3 | 0.59 (c) |
| 12 | m-$NO_2$ | -n-$C_4H_9$ | 43.9 | 0.61 (c) |
| 13 | o-$NO_2$ | -n-$C_4H_9$ | 36.0 | 0.57 (c) |
| 14 | p-$NO_2$ | —$CH(CH_3)_2$ | 78.1 | 0.35 (g) |
| 15 | o-Cl | —$C_2H_5$ | 51.6 | 0.45 (c) |
| 16 | o-Cl | —$CH(CH_3)_2$ | 85.2 | 0.3 (h) |
| 17 | o-Cl | -n-$C_4H_9$ | 72.3 | 0.63 (c) |
| 18 | m-Cl | —$CH_3$ | 81 | 0.25 (h) |
| 19 | m-Cl | —$CH(CH_3)_2$ | 75.8 | 0.31 (h) |
| 20 | m-Cl | —$C_2H_5$ | 56.3 | 0.34 (c) |
| 21 | m-Cl | -n-$C_4H_9$ | 47.7 | 0.51 (c) |

TABLE 1-continued
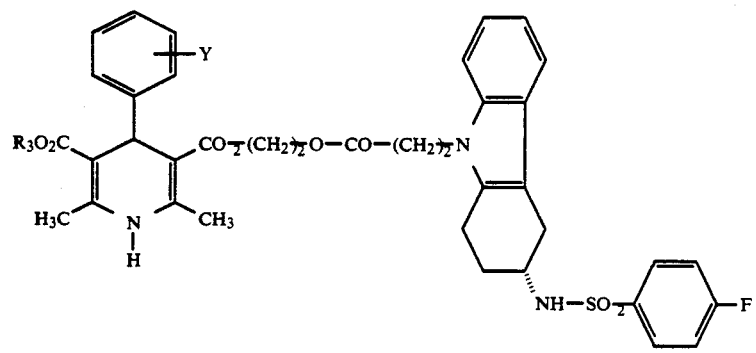
| Ex. No. | Y | $R_3$ | Yield (% of theory) | $R_f$(eluent) |
|---|---|---|---|---|
| 22 | H | $-CH(CH_3)_2$ | 60 | 0.55 (c) |
| 23 | o-$CF_3$ | -n-$C_4H_9$ | 44.3 | 0.62 (c) |
*²separated diastereomers from Ex. 3
TABLE 2
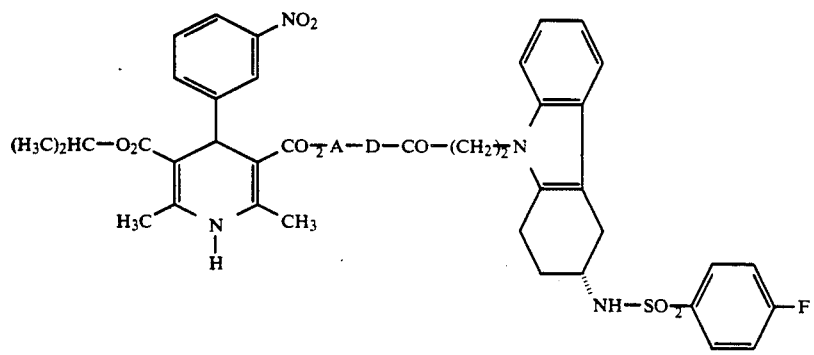
| Ex. No. | A-D | Yield (% of theory) | $R_f$(eluent) |
|---|---|---|---|
| 24 | ~~~O | 67.9 | 0.37 (g) |
| 25 | ~~~~O | 69.4 | 0.41 (g) |
| 26 | (CH₃)₂C-O | 74.3 | 0.57 (g) |
| 27 | neopentyl-O | 61.1 | 0.55 (g) |

TABLE 3

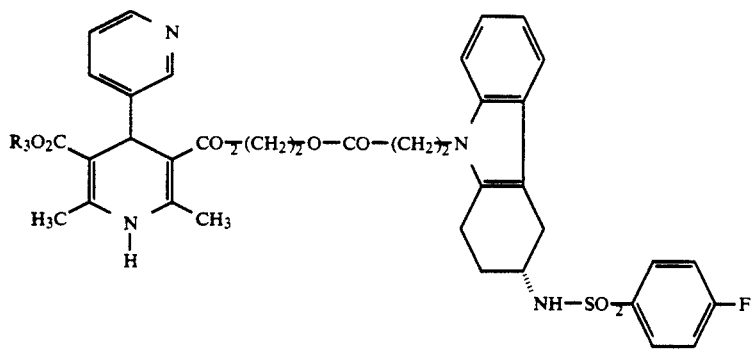

| Ex. No. | R₃ | Yield (% of theory) | R_f (eluent) |
|---|---|---|---|
| 28 | —C₂H₅ | 46.6% | 0.35 (d) |

Method C

General working procedure f or preparation of the compounds of the general formula (I) in which D represents NH, by esterification of various DHP hemi-esters of the general formula (II) with (3R)-3-(4-fluorophenyl-sulphonamido)-1,2,3,4-tetrahydrocarbazole-9-propanoic acid ethanolamide (comp und from Example IV).

7 mmol of DHP hemi-ester and 3.22 g (7 mmol) of the compound from Example IV are dissolved in 20 ml of abs. THF. 100 mg of DMAP and 1.87 g (9.1 mmol) of dicyclohexylcarbodiimide are added at 0° C. The mixture is stirred at 0° C. for 30 min, then at 20° C. for 3 h. The precipitate is filtered off, the THF is distilled off and the residue is taken up in 50 ml of ethyl acetate. The mixture is extracted twice by shaking with saturated aq. Na₂CO₃ solution, once with 1N HCl and once with saturated NaCl solution, and the organic phase is dried over Na₂SO₄ and evaporated. The residue is purified by chromatography (eluent: toluene/acetone mixtures 25:1 to 5:1).

Method D

General working procedure for preparation of the compounds of the general formula (I) in which D represents NH, by reaction of compounds of the general formula (IV, X=NH₂) with (3R)-3-(4-fluorophenylsulphonamido)-1,2,3,4-tetrahydrocarbazole-9-propanecarboxylic acid.

4.16 g (10 mmol) of (3R)-3-(4-fluorophenylsulphonamido)1,2,3,4-tetrahydrocarbazole-9-propanecarboxylic acid, 1.35 g (10 mmol) of N-hydroxy-benzotriazole and 2.27 9 (11 mmol) of dicyclohexylcarbodiimide in 30 ml of abs. THF are stirred at 0° C. for 1 h and at room temperature for 1 h. After addition of 10 mmol of an amine of the general formula IV (X=NH₂), the mixture is additionally stirred at room temperature for 3 h, filtered and the filtrate is evaporated. The residue is dissolved in 50 ml of CH₂Cl₂, and the solution is washed with 1N HCl solution, 1N NAOH solution and said. NaCl solution, dried over Na₂SO₄ and evaporated. The residue is chromatographed on silica gel using toluene/acetone 5:1.

The examples listed in Table 4 are prepared by the general preparation procedures listed above:

TABLE 4

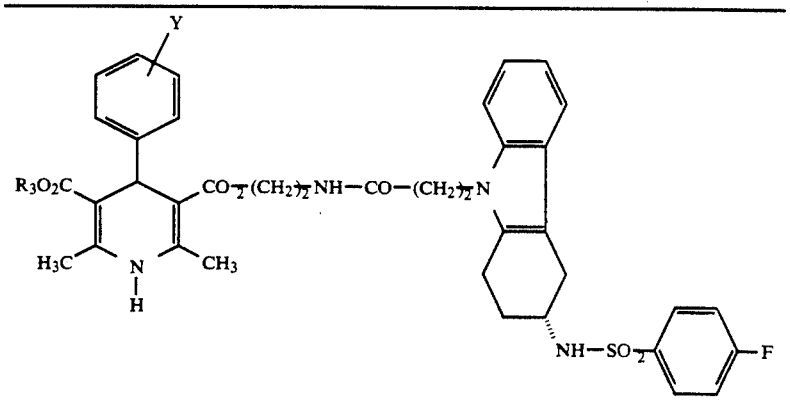

| Ex. No. | Y | R₃ | Yield (% of theory) | R_f (eluent) |
|---|---|---|---|---|
| 29 | m-NO₂ | —CH(CH₃)₂ | 79.1 | 0.46 (h) |
| 30 | m-Cl | —CH(CH₃)₂ | 75 | 0.36 (k) |
| 31 | o-CF₃ | —CH(CH₃)₂ | 54.6 | 0.57 (k) |
| 32 | m-NO₂ | —CH₃ | 72.3 | 0.34 (k) |
| 33 | m-Cl | —CH₃ | 67.5 | 0.29 (k) |
| 34 | o-Cl | —CH₃ | 66.1 | 0.27 (k) |

TABLE 4-continued

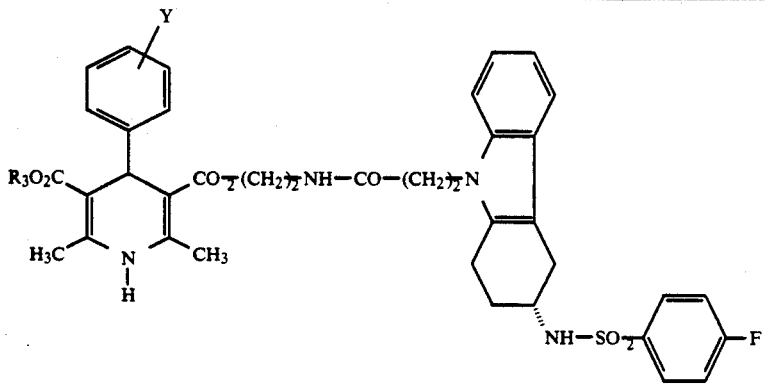

| Ex. No. | Y | $R_3$ | Yield (% of theory) | $R_f$(eluent) |
|---|---|---|---|---|
| 35 | o,m-$Cl_2$ | —$CH_3$ | 73.8 | 0.37 (k) |

We claim:

1. An indolesulphonamide-substituted dihydropyridine of the formula

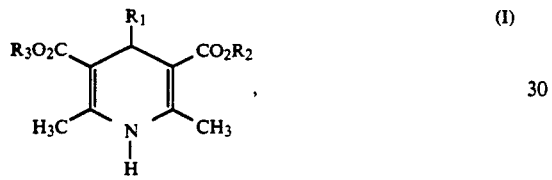

(I)

in which $R_1$ represents phenyl, naphthyl, o-pyridyl, m-pyridyl or p-pyridyl, each of which is optionally monosubstituted or disubstituted by identical or different substituents selected from the group consisting of fluorine, chlorine, bromine, nitro, trifluoromethyl, trifluoromethoxy, straight-chain or branched alkyl or alkoxy each having up to 6 carbon atoms, benzyl and phenoxy, $R_2$ represents a radical of the formula

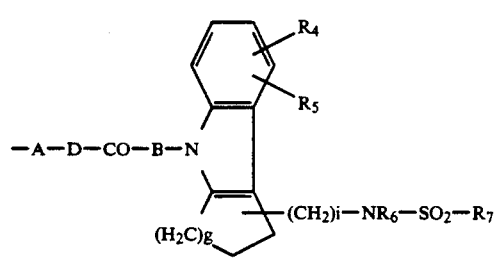

in which

A and B are identical or different and denote a group of the formula —$(CH_2)_b$—$(CR_8R_9)_d$—$(CH_2)_e$, in which b denotes a number 1, 2, 3, or 4, d and e are identical or different and denote a number 0, 1, 2, or 3, $R_8$ and $R_9$ are identical or different and denote hydrogen or straight-chain or branched alkyl having up to 4 carbon atoms, D denotes an oxygen atom or the —NH group, g denotes a number 1 or 2, i denotes a number 0, 1, or 2, $R_4$ and $R_5$ are identical or different and denote hydrogen, phenyl, nitro, cyano, fluorine, chlorine, bromine, trifluoromethyl or straight-chain or branched alkyl, or alkoxy each having up to 4 carbon atoms, $R_6$ denotes hydrogen, straight-chain or branched alkyl having up to 6 carbon atoms $R_7$ denotes phenyl which is optionally monosubstituted or disubstituted by identical or different substituents selected from the group consisting of fluorine, chlorine, trifluoromethyl, trifluoromethoxy, hydroxyl, and carboxyl, or by straight-chain or branched alkoxy, alkyl, or alkoxycarbonyl each having up to 6 carbon atoms or by a group of the formula —$NR_{10}R_{11}$, in which $R_{10}$ and $R_{11}$ are identical or different and denote hydrogen, straight-chain or branched alkyl having up to 4 carbon atoms, phenyl or benzyl, and $R_3$ represents straight-chain or branched alkyl having up to 8 carbon atoms, which is optionally substituted by straight-chain or branched alkoxy, alkylthio, alkoxycarbonyl, acyl or acyloxy each having up to 6 carbon atoms, phenyl, phenoxy, carboxyl or hydroxyl or by the group —$NR_{10}R_{11}$, or a pharmaceutically acceptable salt thereof.

2. An indolesulphonamide-substituted dihydropyridine according to claim 1, in which $R_1$ represents phenyl, naphthyl or m-pyridyl, each of which is optionally monosubstituted or disubstituted by identical or different substituents selected from the group consisting of fluorine, chlorine, nitro, trifluoromethyl, trifluoromethoxy, straight-chain or branched alkyl or alkoxy each having up to 4 carbon atoms, benzyl and phenoxy, $R_2$ represents a radical of the formula

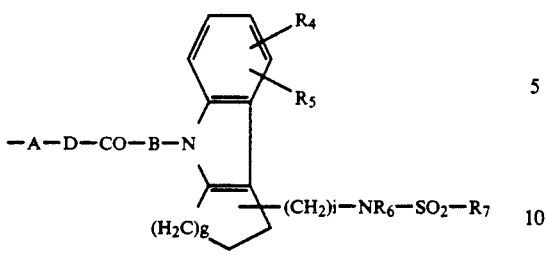

in which

A and B are identical or different and denote a group of the formula —(CH$_2$)$_b$—(CR$_8$R$_9$)$_d$—(CH$_2$)$_e$, in which
- b denotes a number 1, 2, or 3,
- d and e are identical or different and denote a number 0, 1, or 2,
- R$_8$ and R$_9$ are identical or different and denote hydrogen methyl or ethyl, D denotes an oxygen atom or the —NH group,
g denotes a number 1 or 2,
i denotes a number 0 or 1,
R$_4$ and R$_5$ are identical or different and denote hydrogen, phenyl, nitro, fluorine, chlorine, trifluoromethyl or methyl or methoxy,
R$_6$ denotes hydrogen, or straight-chain or branched alkyl having up to 4 carbon atoms,
R$_7$ denotes phenyl which is optionally substituted by fluorine, chlorine, trifluoromethyl, or trifluoromethoxy, or by straight-chain or branched alkoxy, or alkyl, each having up to 4 carbon atoms, and
R$_3$ represents straight-chain or branched alkyl having up to 6 carbon atoms, which is optionally substituted by straight-chain or branched alkoxy, alkylthio, alkoxycarbonyl, or acyl each having up to 4 carbon atoms, phenyl, phenoxy,
or a pharmaceutically acceptable salt thereof.

3. An indolesulphonamide-substituted dihydropyridine according to claim 1, in which R$_1$ represents phenyl or pyridyl, each of which is optionally substituted by fluorine, chlorine, nitro, trifluoromethyl, R$_2$ represents a radical of the formula

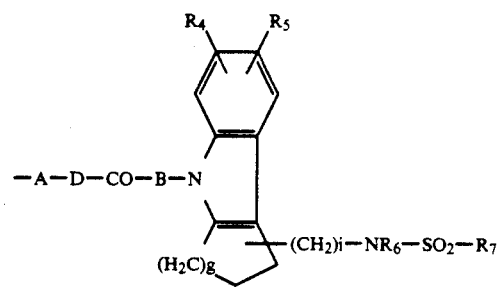

in which

A denotes a group of the formula —(CH$_2$)$_b$—(CR$_8$R$_9$)$_d$—(CH$_2$)$_e$, where
- b represents a number 1, 2, or 3,
- d and e are identical or different and denote a number 0, 1, or 2,
- R$_8$ and R$_9$ are identical or different and denote hydrogen or methyl, D denotes an oxygen atom or an NH group,
g denotes the number 2,
i denotes the number 0,
R$_4$ and R$_5$ denote hydrogen,
R$_6$ denotes hydrogen,
R$_7$ denotes phenyl which is optionally substituted by fluorine, chlorine, and
R$_3$ represents straight-chain or branched alkyl having up to 6 carbon atoms, or a pharmaceutically acceptable salt thereof.

4. A compound according to claim 1, wherein such indolesulphonamide-substituted dihydropyridine is a compound of the formula

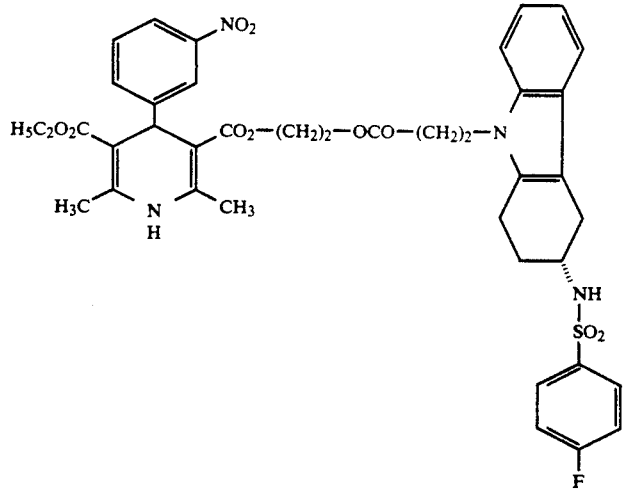

or a pharmaceutically acceptable salt thereof.

5. A compound according to claim 1, wherein such indolesulphonamide-substituted dihydropyridine is a compound of the formula

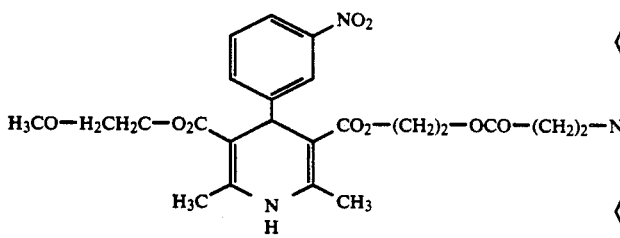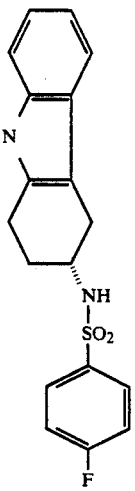
or a pharmaceutically acceptable salt thereof.
6. A compound according to claim 1, wherein such indolesulphonamide-substituted dihydropyridine is a compound of the formula
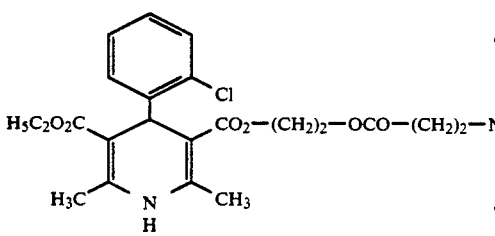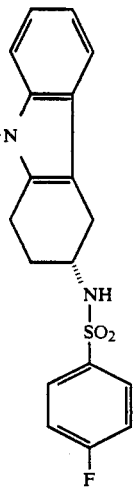
or a pharmaceutically acceptable salt thereof.
7. A compound according to claim 1, wherein such indolesulphonamide-substituted dihydropyridine is a compound of the formula
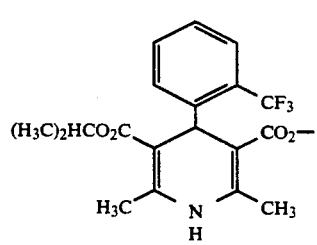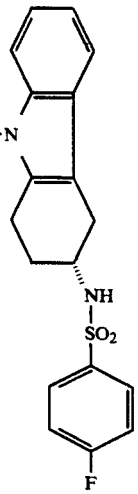

or a pharmaceutically acceptable salt thereof.

8. A composition for the treatment of high blood pressure or inhibiting platelet aggregation, comprising an amount effective therefor of a compound or pharmaceutically acceptable salt thereof according to claim 1 and a pharmacologically acceptable diluent.

9. The method of reducing blood pressure or inhibiting platelet aggregation in a patient in need thereof which comprises administering to such patient an amount effective therefor of a compound or pharmaceutically acceptable salt thereof according to claim 1.

* * * * *

UNITED STATES PATENT AND TRADEMARK OFFICE
CERTIFICATE OF CORRECTION

PATENT NO. : 5,272,161
DATED : December 21, 1993
INVENTOR(S) : Niewohner, et al.

It is certified that error appears in the above-indentified patent and that said Letters Patent is hereby corrected as shown below:

| | |
|---|---|
| Title Page | ABSTRACT: Lines 8-9 delete " thromboedabolic " and substitute -- thromboembolic -- |
| Col. 27, line 21 | After " hydrogen " insert -- , -- |
| Col. 27, lines 26-27 | After " trifluoromethyl " delete " or " and substitute -- , -- |
| Col. 27, line 33 | After " alkoxy " delete " , " |
| Col. 27, line 38 | After " alkoxycarbonyl " delete " , " |
| Col. 28, line 32 | After " fluorine " delete " , " and substitute -- or -- |

Signed and Sealed this

Twenty-second Day of August, 1995

Attest:

BRUCE LEHMAN

*Attesting Officer*          *Commissioner of Patents and Trademarks*